United States Patent [19]

Hardy et al.

[11] Patent Number: 4,587,054

[45] Date of Patent: May 6, 1986

[54] SYNTHESIS OF HYDROPHILIC PHENOL ESTER DERIVATIVES

[75] Inventors: Frederick E. Hardy, Gosforth, England; James E. Thompson, Cincinnati, Ohio

[73] Assignee: The Procter & Gambel Company, Cincinnati, Ohio

[21] Appl. No.: 536,461

[22] Filed: Sep. 26, 1983

[30] Foreign Application Priority Data

Sep. 28, 1982 [GB] United Kingdom ............... 8227674

[51] Int. Cl.$^4$ ........................... C09F 5/08; C09F 7/10
[52] U.S. Cl. .................. 260/410.5; 260/402; 260/404; 560/98; 560/109
[58] Field of Search ............ 260/402, 410.5, 404; 560/98, 109

[56] References Cited

U.S. PATENT DOCUMENTS

| | | | |
|---|---|---|---|
| 2,082,790 | 6/1937 | Cherry | 260/410.5 X |
| 2,134,388 | 10/1938 | Cherry | 260/410.5 |
| 3,413,336 | 11/1968 | Hulsmann, et al. | 260/475 |

FOREIGN PATENT DOCUMENTS

| | | |
|---|---|---|
| 651332 | 12/1964 | Belgium . |
| 864798 | 4/1961 | United Kingdom . |
| 1009484 | 11/1965 | United Kingdom . |
| 2082576 | 3/1982 | United Kingdom . |

OTHER PUBLICATIONS

R. Wagner and H. Zook, *Synthetic Organic Chemistry*, Wiley & Sons, 1953, p. 482.

C. Buehler and D. Pearson, *Survey of Organic Synthesis*, vol. 1, Wiley-Interscience, 1970, pp. 809-811.

W. W. Prichard, *Organic Synthesis*, Coll. vol. 3, p. 452, (1955).

*Primary Examiner*—Helen M. S. Sneed
*Attorney, Agent, or Firm*—Robert B. Aylor; Jerry J. Yetter; Richard C. Witte

[57] ABSTRACT

A hydrophilic phenol ester derivative, especially a sulphonated or carboxylated phenol ester is prepared by reacting a $C_6$-$C_{18}$ substituted or unsubstituted aliphatic carboxylic acid with a $C_2$-$C_3$ alkanoic anhydride, and reacting the resultant $C_6$-$C_{18}$ acid anhydride with a substituted phenol such as an alkali metal phenol sulphonate salt or hydroxybenzene carboxylic acid to give a $C_6$-$C_{18}$ acyloxy derivative of a substituted benzene. The two stage process may be carried out in the same reaction vessel without the use of solvents. The products are useful as peroxyacid bleach precursors.

8 Claims, No Drawings

SYNTHESIS OF HYDROPHILIC PHENOL ESTER DERIVATIVES

FIELD OF THE INVENTION

This invention relates to the acylation of hydrophilic phenol derivatives and more especially to a method of acylating a sulphonated or carboxylated phenol. Sulphonated and carboxylated phenol esters comprise a class of materials suitable for use in detergent compositions as so-called bleach activators, more correctly characterized as organic peroxy acid precursors. These precursors react in aqueous solution with the inorganic peroxygen bleaches such as perborate or percarbonate normally incorporated in detergent compositions, to form organic peroxy acids which are much more effective bleaches than the inorganic peroxy salts at low temperatures (<70° C.).

BACKGROUND OF THE INVENTION

The conventional method of synthesizing substituted phenol ester involves the acylation in a solvent such as hexane or dichloroethane, of a salt of the substituted phenol with an acyl halide, (normally the chloride), eliminating hydrogen halide. This method, however, suffers from several disadvantages. The starting acyl halide is itself a difficult and unpleasant material to handle in bulk, and the equipment needed to withstand corrosive attack by the hydrogen halide byproduct of the reaction is expensive. A further problem arises in the elimination of the hydrogen halide from the reaction system. This is normally carried out by means of an inert gas sparging system but the tendency of the suspended solid reaction product to cause foaming of the reaction mixture, and the need to avoid removal of the solvent and/or the acyl halide, restricts the gas flow rate, and thus the completeness of removal. If HCl is not removed efficiently there is competition with the sulphonate group for sodium ions leading to sodium chloride and a less stable sulphonic acid form of the product.

An alternative synthesis route involves the preparation of the appropriate alkanoic anhydride, normally by means of a reaction between acetic anhydride and the appropriate carboxylic acid, followed by the further reaction of the alkanoic anhydride with the substituted phenol ester. In conventional practice, the two reaction stages are carried out separately. In the first stage the carboxylic acid and acetic anhydride, the latter being employed in excess and serving as a reaction medium, are refluxed from 6-8 hours and the unreacted acetic anhydride is then distilled off together with any acetic acid formed during the reaction. The alkanoic anhydride is then isolated by fractional distillation before being reacted with the substituted phenol ester.

The applicants have now found that the preparation of hydrophilic substituted phenol esters can be simplified by carrying out both reactions in a single reactor and by employing a catalyst, preferably of strong acid type, to reduce the severity of the reaction conditions.

According to the present invention there is provided a method of preparing a substituted phenol ester comprising the steps of:

(a) reacting a $C_2$-$C_3$ alkanoic anhydride with a substituted or unsubstituted $C_6$-$C_{18}$ aliphatic carboxylic acid in a molar ratio of anhydride:acid of at least 0.5:1;

(b) volatilizing and removing the excess $C_2$-$C_3$ alkanoic anhydride and any $C_2$-$C_3$ carboxylic acid formed during the reaction, whilst maintaining the $C_6$-$C_{18}$ acid anhydride in a fluid state;

(c) reacting the $C_6$-$C_{18}$ acid anhydride with a substituted phenol in the presence of a strong acid or base catalyst, the substituted phenol having the general formula

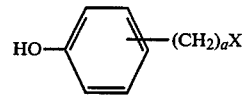

wherein X is selected from
(i) —COOH
(ii) —OSO$_3$M
(iii) —SO$_3$M
(iv)

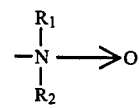

(v) —N$^+$R$_1$R$_2$R$_3$Y$^-$ wherein M is alkali metal or alkaline earth metal, each of R$_1$, R$_2$ and R$_3$ is a C$_1$-C$_3$ alkyl group, a is 0 or 1 and Y is a hydrophilic group selected from halide, methosulphate and ethosulphate radicals; and (d) recovering the substituted $C_6$-$C_{18}$ acyloxy benzene from the reaction mixture.

In a preferred embodiment of the process, the substituted $C_6$-$C_{18}$ acyloxybenzene is a $C_6$-$C_{10}$ acyloxybenzene sulphonate and the catalyst is a strong acid catalyst such as H$_2$SO$_4$. Preferably the $C_6$-$C_{18}$ aliphatic carboxylic acid byproduct from the second stage of the reaction is recovered and recycled to the first stage of the reaction.

DETAILED DESCRIPTION OF THE INVENTION

The present invention relates to a two stage process for the preparation of substituted phenol esters in which a $C_2$-$C_3$ alkanoic anhydride is reacted with a $C_6$-$C_{18}$ aliphatic carboxylic acid and a substituted phenol is then added to the reaction product to give the substituted $C_6$-$C_{18}$ acyloxy benzene. The $C_6$-$C_{18}$ aliphatic carboxylic acid may itself be substituted or unsubstituted.

Substituted phenols, to which the process of the invention can be applied, have the formula

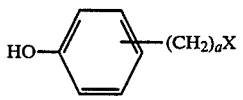

wherein X can be
(i) —COOH
(ii) —OSO$_3$M
(iii) —SO$_3$M
(iv)

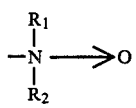

(v) $-N^+R_1R_2R_3Y^-$ wherein M is alkali metal, or alkaline earth metal, each of $R_1$, $R_2$ and $R_3$ is a $C_1$–$C_3$ alkyl group, a is 0 or 1 and Y is a hydrophilic group selected from halide, methosulphate and ethosulphate radicals.

Where a is 0 in substituents (iv) and (v), X is preferably in the 3- or m-position, but where a is 1 in (iv) and (v) and for substituents (i), (ii) and (iii), regardless of the value of a, the substituent is preferably in the 4- or p-position.

Preferred substituted phenols are those in which a is 0 and X is (i) or (iii) with M being sodium, and also where a is 1 and X is (v) with $R_1$ and $R_2$ being methyl.

The carboxylic acids utilized in the process of the invention are substituted or unsubstituted aliphatic carboxylic acids containing from about 6 to about 18 carbon atoms and can be acyclic or ring-containing in type; the acyclic acids can be linear or non-linear and the ring structure may be either alicyclic or aromatic, an example of the latter being hydrocinnamic acid (3-phenyl propionic acid). The carboxylic acids preferably contain from 6 to 12 carbon atoms, and most preferably from about 8 to about 10 carbon atoms, the preferred acids having at least five carbon atoms including the carbonyl carbon arranged in a linear or substantially linear configuration. 'Substantially linear' is intended to refer to a hydrocarbyl moiety having no more than approximately 25% methyl branching. Linear aliphatic carboxylic acids can be synthetic or natural in origin, a preferred source of linear $C_8$–$C_{10}$ carboxylic acid being the 'light' fraction of coconut fatty acid, composed principally of a mixture of $C_8$ and $C_{10}$ fatty acids. Non-linear aliphatic carboxylic acids are produced by synthetic techniques, such as those disclosed in Kirk-Othmer Encyclopaedia of Chemical Technology 3rd Edition 4 pp 861–863.

Although both acetic and propionic anhydrides can be used in the process of the invention, acetic anhydride is highly preferred for reasons of reactivity, availability, cost and ease of processing. Acid anhydrides in which the acyl group has 3 carbon atoms are insufficiently reactive for the purposes of the invention.

In accordance with the invention a catalyst is used in the second stage of the reaction to reduce the severity of the reaction conditions and is preferably also used in the first stage to reduce the reaction time for formation of the $C_6$–$C_{18}$ acid anhydride. Both strong acid and base catalysts can be employed. Strong acid catalysts such as sulphuric acid, perchloric acid, fluorosulphonic acid, tri-fluoromethylsulphonic acid and toluenesulphonic acid are preferred. Catalyst is normally added in an amount of from about 0.1% to about 5% based on the weight of substituted phenol.

In the process according to the broadest aspect of the invention the $C_6$–$C_{18}$ carboxylic acid is mixed or dissolved in the $C_2$–$C_3$ alkanoic anhydride to form a clear solution which is heated under reflux conditions ($\approx 140°$ C.) to form the $C_6$–$C_{18}$ acid anhydride.

In one aspect of this stage of the process of the invention, a considerable excess of acetic anhydride is used relative to that required stoichiometrically (acid:anhydride=2:1 molar). Molar ratios of anhydride to acid of at least about 3:1 and more conveniently in the range from about 4:1 to about 6:1 permit the employment of the anhydride as a reaction medium. This maximizes the formation of a $C_6$–$C_{18}$ acid anhydride whilst keeping the formation of mixed $C_2$–$C_3$—$C_6$–$C_{18}$ acid anhydride to a minimum but requires a relatively long reaction time (6–8 hours). In another aspect of the process, approximately stoichiometric quantities of $C_6$–$C_{18}$ aliphatic carboxylic acid and $C_2$–$C_3$ alkanoic anhydride are used (viz. a molar ratio of about 2:1), which leads to $C_6$–$C_{18}$ carboxylic acid remaining unconverted at the end of the reaction. However, the reaction time is shorter (2–3 hours) and the presence of unreacted $C_6$–$C_{18}$ carboxylic acid is not believed to be a disadvantage in a "one pot" reaction, as $C_6$–$C_{18}$ carboxylic acid is itself formed as a by-product in the second stage of the process and serves as an additional reaction medium therefor.

The progress of the reaction to form $C_6$–$C_{18}$ acid anhydride can be followed by GLC analysis, and when complete, reflux is discontinued and the excess $C_2$–$C_3$ alkanoic anhydride is removed by distillation under reduced pressure (10–25 mm Hg) at a temperature in the range 40° C.–100° C. This also removes the $C_2$–$C_3$ carboxylic acid byproduct and any mixed anhydride which has formed during the reaction. Typical yields of the $C_6$–$C_{18}$ acid anhydride are in the range from about 90 to about 95% although the anhydride is not isolated but is retained in the reactor for the second stage of the process.

The $C_6$–$C_{18}$ acid anhydride is then raised to a temperature at which it is in liquid state in order to allow dispersion therein of the ingredients for the second stage of the process. Anhydrides of carboxylic acids containing from about 6 to about 9 carbon atoms are liquid at ambient temperatures whereas those of acids having from about 10 to about 18 carbon atoms in the molecule require heating to make them liquid and heating to a temperature of about 75° C. maximum is adequate for this purpose.

The substituted phenol and the catalyst are then added to the anhydride and dispersed therein. The molar ratio of the anhydride to the substituted phenol is normally close to 1:1 but can be varied in the range from about 0.75:1 to about 1.5:1. The reaction completeness and the product purity tend to be enhanced by an excess of anhydride but too large an excess requires subsequent recovery of the unreacted anhydride. Conversely an excess of the substituted phenol, although permitting efficient usage of the anhydride, may give rise to lower than optimum product purity arising from difficulties in separating unreacted substituted phenol from the reaction product. In general, a slight excess of anhydride e.g. about 1.1–1.25× molar, is preferred.

Most of the substituted phenols useful in the process of the invention are only slightly soluble in the anhydride and will remain primarily in the form of dispersed solids. These dispersed solid materials must be finely divided in order to maximize the surface area available for reaction. Preferably the solids should be less than 100 microns in particle size, more preferably less than 50 microns and ideally should be as fine as possible. Conventional comminution techniques can be used in order to achieve the desired particle size.

The reaction mixture is then heated with agitation for about 1–6 hours at a temperature dependent on the catalyst system employed. Basic catalysts require a temperature in the range from about 180° to about 220°

C. whilst strong acid catalysts employ milder conditions of from about 80° to about 120° C. The reaction mixture thickens as the reaction progresses but does not solidify completely as, for every mole of anhydride that reacts, a mole of carboxylic acid is released and serves as a fluid medium. Progress of the reaction can be monitored by GLC determination of the ratio of $C_6$–$C_{18}$ carboxylic acid to anhydride. When the reaction is complete the reactor contents are dispersed in diethyl ether or petroleum ether and the solid product recovered by filtration. The byproduct $C_6$–$C_{18}$ carboxylic acid can be recovered from the filtrate by evaporation of the solvent, recycling both solvent and carboxylic acid to their respective points of use in the process.

The process of the invention can be illustrated by the reaction of nonanoic acid with acetic anhydride to form nonanoic anhydride which in turn is reacted with a substituted phenol.

Preparation of Nonanoic Anhydride

A 1000 ml flask was charged with 158 g nonanoic acid (1 mole) and 306 g acetic anhydride (3.8 moles). The flask was fitted with a conventional overhead condenser and distillate collection vessel which was also connected to a water pump capable of providing a reduced pressure of 10-25 mm mercury in the system. The mixture formed a clear mobile solution and was heated to 150° C. under reflux at atmospheric pressure for eight hours. Reflux was then discontinued and the condenser adjusted to permit the volatile components of the reaction mixture to be distilled. Heating was reduced and the water pump was turned on to reduce the system vapor pressure to 15 mm mercury and the excess acetic anhydride, byproduct acetic acid and a small quantity of mixed acetic-nonanoic anhydride were removed at a reactor temperature of 40° C. to 100° C.

When distillate collection had ceased, the vacuum was released and heating discontinued. The product was a pale yellow liquid which was mobile at ambient temperature (20° C.). GLC analysis showed the product to be 94% nonanoic anhydride.

Acid Catalyzed Preparation of Sodium Nonanoyl Oxybenzene Sulphonate 10 g (0.034 mole) of the nonanoic anhydride product was then added to a 250 ml stirred flask and 5.3 g (0.027 mole) sodium phenol sulphonate of particle size $<100\mu$, together with 0.18 g (0.0018 mole) sulphuric acid was dispersed therein. The mole ratio of anhydride:sulphonate was 1.24:1. The temperature was raised to 90°–100° C. and maintained at that value for four hours during which time the consistency of the reaction mixture thickened considerably. After this time the reactor contents were cooled to 40° C. and dispersed in 200 ml diethyl ether. The solid was filtered off and subjected to two further washes before being dried and analysed to give 12.90 g of sodium nonanoyloxybenzene sulphonate (yield=96% based on the phenol sulphonate). NMR analysis showed a purity of 97%.

Acid Catalyzed Preparation of Sodium Nonanoyloxybenzoate 12.5 g (0.042 mole) of the nonanoic anhydride product prepared above was added to a 250 ml stirred flask and 4.70 g (0.034 mole) p-hydroxybenzoic acid (mole ratio of anhydride:acid=1.24:1) and 0.13 g (0.0013 mole) sulphuric acid added to the anhydride to form a mobile dispersion. This was heated to 90°–100° C. and maintained at this temperature for 3 hours before being cooled to 40° C. and dispersed in 200 ml petroleum ether. After filtration the solid was subjected to two further washes before being dried and analyzed to give a yield of 80%, based on the p-hydroxybenzoic acid, and a purity of 99+%.

Acid Catalyzed Preparation of Sodium Nonanoyl Oxybenzene Sulphonate with Product Heel 29.8 g (0.10 mole) nonanoic anhydride, 17.6 g (0.090 mole) anhydrous sodium phenol sulphonate, (mole ratio of anhydride:sulphonate=1.11:1), 0.1 g (0.001 mole) sulphuric acid and 1.5 g (0.0045 mole) previously formed sodium nonanoyloxybenzene sulphonate were added to a 250 ml three necked flask. The flask was fitted with a mechanical stirrer and an argon gas feed to provide an inert atmosphere and was immersed in a temperature controlled oil bath set at 100° C. Agitation was started and the flask heated for two hours. The flask contents became progressively thicker and after 30-45 minutes were no longer effectively mixed by the stirrer although agitation was maintained throughout the two hour period. At the end of the reaction period the flask was allowed to cool and the contents mixed with 100 ml diethyl ether and filtered. The precipitate was washed twice with 150 ml portions of ether and then vacuum dried. The white powder product weight 31.0 g (97.7% based on sodium phenol sulphonate) and NMR spectroscopic analysis gave a purity >99%.

Base Catalyzed Preparation of Sodium Nonanoyl Oxybenzene Sulphonate with Product Heel 95 g (0.31 mole) nonanoic anhydride, 56.8 g (0.29 mole) anhydrous sodium phenol sulphonate (mole ratio of anhydride:sulphonate=1.07:1), 0.216 g (0.004 mole) sodium methoxide in xylene (0.09/ml) and 4.2 g (0.0125 mole) previously formed sodium nonanoyl oxybenzene sulphonate were added to a 1000 ml flask. The flask was fitted with an agitator and an argon gas feed to provide an inert atmosphere and was immersed in a temperature-controlled oil bath set at 200° C. The contents of the flask were heated and stirred for two hours during which time they thickened to a pasty solid. After two hours the flask was allowed to cool, 100 ml diethyl ether was added to the contents and stirred and the mixture was then filtered. The filtered solids were washed twice with an additional 150 ml ether and were then vacuum dried to give 97.2 g of a white solid product, a yield of 95.6% based on the sodium phenol sulphonate. NMR spectroscopic analysis showed the purity of the product to be >99%.

We claim:

1. A method of preparing a substituted phenol ester comprising the steps of:
   (a) reacting a $C_2$–$C_3$ alkanoic anhydride with a linear or nonlinear, cyclic or acyclic unsubstituted $C_6$–$C_{18}$ aliphatic carboxylic acid in a molar ratio of anhydride:acid of at least 0.5:1;
   (b) volatilizing and removing the excess $C_2$–$C_3$ alkanoic anhydride and any $C_2$–$C_3$ carboxylic acid formed during the reaction, whilst maintaining the $C_6$–$C_{18}$ acid anhydride in a fluid state;
   (c) reacting the $C_6$–$C_{18}$ acid anhydride with a substituted phenol at temperatures between about 80° and about 120° C. in the presence of a strong acid catalyst, or at temperatures between about 180° and about 220° C. in the presence of a base catalyst, the substituted phenol having the general formula

wherein X is selected from
(i) —COOH
(ii) —OSO$_3$M
(iii) —SO$_3$M
(iv)

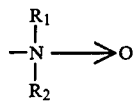

(v) —N$^+$R$_1$R$_2$R$_3$Y$^-$ wherein M is alkali metal, or alkaline earth metal, each of R$_1$, R$_2$ and R$_3$ is a C$_1$-C$_3$ alkyl group, a is 0 or 1 and Y is a hydrophilic group selected from halide, methosulphate and ethosulphate radicals; and (d) recovering the substituted C$_6$-C$_{18}$ acyloxy benzene from the reaction mixture.

2. A method according to claim 1 wherein the molar ratio of the C$_6$-C$_{18}$ acid anhydride to the substituted phenol in step (c) is in the range from 0.75:1 to 1.5:1.

3. A method according to claim 1 wherein the catalyst is selected from the group consisting of sulphuric, toluene sulphonic, and perchloric acid.

4. A method according to claim 3 wherein the catalyst is added to the first stage of the reaction.

5. A method according to claim 1 wherein the substituted phenol is selected from the group consisting of sodium phenol sulphonate and p-hydroxybenzoic acid.

6. A method of preparing a substituted phenol ester comprising the steps of:
(a) reacting acetic anhydride with a linear or nonlinear, cyclic or acyclic unsubstituted C$_8$-C$_{10}$ aliphatic carboxylic acid in a molar ratio of anhydride:acid of at least about 3:1;
(b) volatilizing and removing the excess acetic anhydride and any acetic acid forming during the reaction, whilst maintaining the C$_8$-C$_{10}$ acid anhydride in a fluid state;
(c) adding to said fluid reaction medium:
(i) a substituted phenol having the general formula

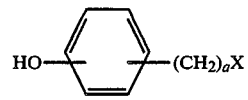

wherein X is selected from the group consisting of
(i) —COOH
(ii) —SO$_3$M
wherein M is an alkali metal and a is 0 or 1, said substituted phenol being in the form of a finely divided solid of particle size <100 microns, the molar ratio of the C$_8$-C$_{10}$ acid anhydride to the substituted phenol being in the range from about 0.75:1 to about 1.5:1,
(ii) from about 0.1% to about 0.5% by weight of the substituted phenol of a strong acid catalyst selected from sulphuric, perchloric, fluorosulphonic, trifluorosulphonic and toluene sulphonic acids,
(d) reacting said substituted phenol with said C$_8$-C$_{10}$ acid anhydride for a period of from about 1 to about 6 hours at temperatures between about 80° C. and about 120° C., and
(e) recovering the substituted C$_8$-C$_{10}$ acyloxy benzene from the reaction mixture.

7. A method according to claim 6 wherein the molar ratio of the C$_8$-C$_{10}$ acid anhydride to the substituted phenol in step (c) is in the range from about 1.1:1 to about 1.25:1.

8. A method of preparing a substituted phenol ester according to claim 1 in which the aliphatic carboxylic acid used is a linear or nonlinear, cyclic or acyclic unsubstituted C$_6$-C$_{12}$ aliphatic carboxylic acid.

* * * * *